(12) United States Patent
Kang et al.

(10) Patent No.: US 11,058,402 B2
(45) Date of Patent: Jul. 13, 2021

(54) HEARTBEAT DETECTION SIGNAL PROCESSING METHOD FOR ULTRASOUND DOPPLER FETUS MONITORING DEVICE

(71) Applicant: BISTOS CO., LTD., Seongnam-si (KR)

(72) Inventors: Chung Shin Kang, Suwon-si (KR); Seong Ill Ko, Yongin (KR)

(73) Assignee: BISTOS CO., LTD., Seongnam-si (KR)

( * ) Notice: Subject to any disclaimer, the term of this patent is extended or adjusted under 35 U.S.C. 154(b) by 333 days.

(21) Appl. No.: 15/774,679

(22) PCT Filed: Dec. 23, 2015

(86) PCT No.: PCT/KR2015/014206
§ 371 (c)(1),
(2) Date: May 9, 2018

(87) PCT Pub. No.: WO2017/082461
PCT Pub. Date: May 18, 2017

(65) Prior Publication Data
US 2018/0325494 A1 Nov. 15, 2018

(30) Foreign Application Priority Data
Nov. 11, 2015 (KR) .................. 10-2015-0158330

(51) Int. Cl.
*A61B 8/08* (2006.01)
*A61B 8/02* (2006.01)
(Continued)

(52) U.S. Cl.
CPC .............. *A61B 8/5223* (2013.01); *A61B 8/02* (2013.01); *A61B 8/08* (2013.01); *A61B 8/0866* (2013.01);
(Continued)

(58) Field of Classification Search
CPC ........... A61B 8/5223; A61B 8/08; A61B 8/02; A61B 8/0866; A61B 8/488; A61B 8/5269; A61B 5/024; A61B 5/4362; G16H 50/30
See application file for complete search history.

(56) References Cited

U.S. PATENT DOCUMENTS 5,069,218 A * 12/1991 Ikeda .................. A61B 8/467
 600/483
6,375,621 B1 * 4/2002 Sullivan ................ A61B 5/113
 600/484
(Continued)

FOREIGN PATENT DOCUMENTS

KR 1020070057630 1/2009
KR 1020140092099 * 7/2014

*Primary Examiner* — Christopher Koharski
*Assistant Examiner* — Kaitlyn E Selmer
(74) *Attorney, Agent, or Firm* — PatentFile, LLC; Bradley C. Fach; Steven R. Kick (57) ABSTRACT

Provided is a heartbeat detection signal processing method of an ultrasonic Doppler fetus monitoring device that transmits an ultrasonic wave to the abdomen of a pregnant woman and detects a fetal heartbeat rate by receiving a Doppler variation signal generated according to the fetal heartbeat. The method includes: receiving (S01) a Doppler signal according to a heartbeat, after removing (S02) a noise from the received Doppler signal, after transmitting (S03) it through a band-pass filter, and preprocessing (S04) it to extract an effective signal of the Doppler signal using a moving window average to select a signal of the input Doppler shifted frequency band; calculating a fetal heartbeat rate through an Average Magnitude Difference Function (AMDF) (S05a), an Autocorrelation Function (S05b), and a weighted autocorrelation function (S05c) using the Average Magnitude Difference Function (AMDF) and the Autocorrelation Function to detect a periodicity of a signal that (Continued)

varies according to the heartbeat from the selected signal; configuring (S06) a histogram using each heartbeat rate calculated through the Average Magnitude Difference Function (AMDF), the Autocorrelation Function, and the Weighted Autocorrelation Function; and estimating and determining a fetal heartbeat rate according to a maximum frequency value in the histogram to display it (S07), wherein after a threshold of the noise signal is estimated in the preprocessing (S04) it using the moving window average, it is used again as a noise signal threshold in the removing (S02) of the noise.

5 Claims, 10 Drawing Sheets

(51) Int. Cl.
*A61B 5/024* (2006.01)
*A61B 5/00* (2006.01)

(52) U.S. Cl.
CPC ............ *A61B 8/488* (2013.01); *A61B 8/5269* (2013.01); *A61B 5/024* (2013.01); *A61B 5/4362* (2013.01)

(56) References Cited

U.S. PATENT DOCUMENTS

| | | | |
|---|---|---|---|
| 2005/0267377 A1* | 12/2005 | Marossero | A61B 5/02411 600/511 |
| 2008/0269625 A1* | 10/2008 | Halperin | A61B 5/6892 600/508 |
| 2010/0137727 A1* | 6/2010 | Sameni | A61B 5/4362 600/511 |
| 2010/0191118 A1* | 7/2010 | Kabakov | A61B 8/02 600/453 |
| 2010/0274145 A1* | 10/2010 | Tupin, Jr. | A61B 5/7278 600/511 |
| 2013/0123637 A1* | 5/2013 | Wohlschlager | G01S 7/526 600/453 |
| 2013/0245436 A1* | 9/2013 | Tupin, Jr. | G01S 13/88 600/430 |

* cited by examiner

HEARTBEAT DETECTION SIGNAL PROCESSING METHOD FOR ULTRASOUND DOPPLER FETUS MONITORING DEVICE

This Application is a 35 U.S.C. 371 National Stage Entry of International Application No. PCT/KR2015/014206 filed on Dec. 23, 2015, which claims the benefit of Republic of Korea Patent Application No. 10-2015-0158330, filed on Nov. 11, 2015, the entire disclosures of which are incorporated by reference herein.

BACKGROUND

The present disclosure relates to a heartbeat detection signal processing method of an ultrasonic Doppler fetus monitoring device that transmits an ultrasonic wave to the abdomen of a pregnant woman and detects a fetal heartbeat rate by receiving a Doppler variation signal generated according to the fetal heartbeat, the method including: receiving (S01) a Doppler signal according to a heartbeat, after removing (S02) a noise from the received Doppler signal, after transmitting (S03) it through a band-pass filter, and preprocessing (S04) it to extract an effective signal of the Doppler signal using a moving window average to select a signal of the input Doppler shifted frequency band; calculating a fetal heartbeat rate through an Average Magnitude Difference Function (AMDF) (S05a), an Autocorrelation Function (S05b), and a weighted autocorrelation function (S05c) using the Average Magnitude Difference Function (AMDF) and the Autocorrelation Function to detect a periodicity of a signal that varies according to the heartbeat from the selected signal; configuring (S06) a histogram using each heartbeat rate calculated through the Average Magnitude Difference Function (AMDF), the Autocorrelation Function, and the Weighted Autocorrelation Function; and estimating and determining a fetal heartbeat rate according to a maximum frequency value in the histogram to display it (S07), wherein after a threshold of the noise signal is estimated in the preprocessing (S04) using the moving window average, the threshold is used again as a noise signal threshold in the removing (S02) of the noise.

Fetal diagnosis is performed during the pregnancy period or during delivery to cope with emergency conditions such as fetal status check and lack of oxygen supply. In particular, a fetal monitor is a device that evaluates the fetal well-being by non-invasively measuring the uterine contraction and fetal heartbeat rate during pregnancy.

Methods for measuring fetal heartbeat rate include a method for using ultrasound Doppler and a method for measuring fetal electrocardiogram.

The method for using ultrasonic Doppler is a method for detecting a fetal heartbeat rate by using the Doppler effect in which the ultrasound irradiated to the abdomen of the mother is reflected from the heart of the fetus. The fetal heartbeat rate detection method using ultrasonic Doppler is easy to detect fetal heartbeat in early pregnancy but it is not sensitive enough to show heartbeat rate variability. In addition, fetal heartbeat rate is detected half or double, or is cross-measured with the mother's heartbeat rate so that there is an error between the heart sound and the calculated heartbeat rate.

As one of the causes of fetal heartbeat rate measurement error, there may be an error in fetal heartbeat rate detection from ultrasound Doppler signal. For example, there is a problem that a peak detection accuracy may be reduced and an error may occur in the process of performing peak detection in order to detect a fetal heartbeat period from an ultrasonic Doppler signal.

On the other hand, as a method for more accurately detecting a peak value from such a signal value, there is known a method of using an Average Magnitude Difference Function (AMDF) in the "Pitch correction method in an AMDF pitch search device" (Korean Patent Laid-Open No. 10-2004-0028293) and in the "Peak detection method, peak detection device, and fetal heartbeat detection device" (Korean Patent Laid-Open Publication No. 10-2014-0092099) of the following patent document 2, a technique using various functions including an Average Magnitude Difference Function (AMDF) is disclosed for heartbeat detection of a fetus.

However, in the case of these existing technologies, inaccurate peak values may be found in an environment with noisy and weak tones. Accordingly, the reliability may not be known and the error value may be determined as a true value.

SUMMARY

By solving the problems of the above-described conventional methods in order to improve the peak detection accuracy and lower the fetal heartbeat detection error, the present invention is to provide a method for processing a heartbeat detection signal of an ultrasonic Doppler fetus monitoring device using a preprocessing method, a peak detection method, a probabilistic estimation value determination, and a reliability estimation.

The present invention is to provide a fetal heartbeat detecting device for obtaining accurate true values considering the statistics and various periodic measurement algorithms for the waveforms extracted from the fetal heart sound measurement device and calculating the reliability of the estimation for each estimation result.

Meanwhile, in the present invention, the measured heartbeat rate change is spectrum-analyzed through frequency analysis using fast Fourier transform (FFT) with a window of 5 to 10 minutes in size, and the distribution and size of the dynamic change according to the frequency band (Very Low Frequency (VLF), Low Frequency (LF), Medium Frequency (MF), and High Frequency (HF)) of the heartbeat rate change is known so that useful information for fetal health examination may be obtained together.

In accordance with an exemplary embodiment of the present invention, provided is a heartbeat detection signal processing method of an ultrasonic Doppler fetus monitoring device that transmits an ultrasonic wave to the abdomen of a pregnant woman and detects a fetal heartbeat rate by receiving a Doppler variation signal generated according to the fetal heartbeat. The method includes: receiving (S01) a Doppler signal according to a heartbeat, after removing (S02) a noise from the received Doppler signal, after transmitting (S03) it through a band-pass filter, and preprocessing (S04) it to extract an effective signal of the Doppler signal using a moving window average to select a signal of the input Doppler shifted frequency band; calculating a fetal heartbeat rate through an Average Magnitude Difference Function (AMDF) (S05a), an Autocorrelation Function (S05b), and a weighted autocorrelation function (S05c) using the Average Magnitude Difference Function (AMDF) and the Autocorrelation Function to detect a periodicity of a signal that varies according to the heartbeat from the selected signal; configuring (S06) a histogram using each heartbeat rate calculated through the Average Magnitude Difference Function (AMDF), the Autocorrelation Function, and the Weighted Autocorrelation Function; and estimating and determining a fetal heartbeat rate according to a maximum frequency value in the histogram to display it (S07), wherein after a threshold of the noise signal is estimated in the preprocessing (S04) using the moving window average, the threshold is used again as a noise signal threshold in the removing (S02) of the noise.

The method may further include calculating and displaying a measurement reliability as a δ value determined according to the following equation in the histogram.

[Equation] where the δ represents the standard deviation and $\overline{x}$ is the mean value of the data set and X is a data point from the data set and N is the total number of data points.

$$\delta = \sqrt{\frac{\sum |x - \overline{x}|^2}{N}}$$

The Weighted Autocorrelation Function may be determined by multiplying the reciprocal of the Average Magnitude Difference Function (AMDF) and the Autocorrelation Function.

A window size and a movement interval for peak detection may be dynamically updated based on a previous signal period.

The window size may be set at intervals of 5 to 10 minutes, wherein a distribution and a size according to a frequency band of the heartbeat rate may be further detected by spectrum-analyzing each heartbeat rate calculated through the Average Magnitude Difference Function (AMDF), the Autocorrelation Function, and the Weighted Autocorrelation Function, through fast Fourier transform (FFT).

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Hereinafter, a heartbeat detection signal processing method of an ultrasonic Doppler fetus monitoring device according to an embodiment of the present invention will be described in detail with reference to the accompanying drawings. First, in the drawings, it should be aware that the same components or parts are denoted by the same reference numerals whenever possible. In describing the present invention, a detailed description of related known functions and configurations will be omitted so as not to obscure the subject matter of the present invention.

A heartbeat detection signal processing method of an ultrasonic Doppler fetus monitoring device according to an embodiment of the present invention relates to a heartbeat detection signal processing method of an ultrasonic Doppler fetus monitoring device that transmits an ultrasonic wave to the abdomen of a pregnant woman and receives a Doppler variation signal generated according to a fetal heartbeat to detect a fetal heartbeat rate.

Figure 1:
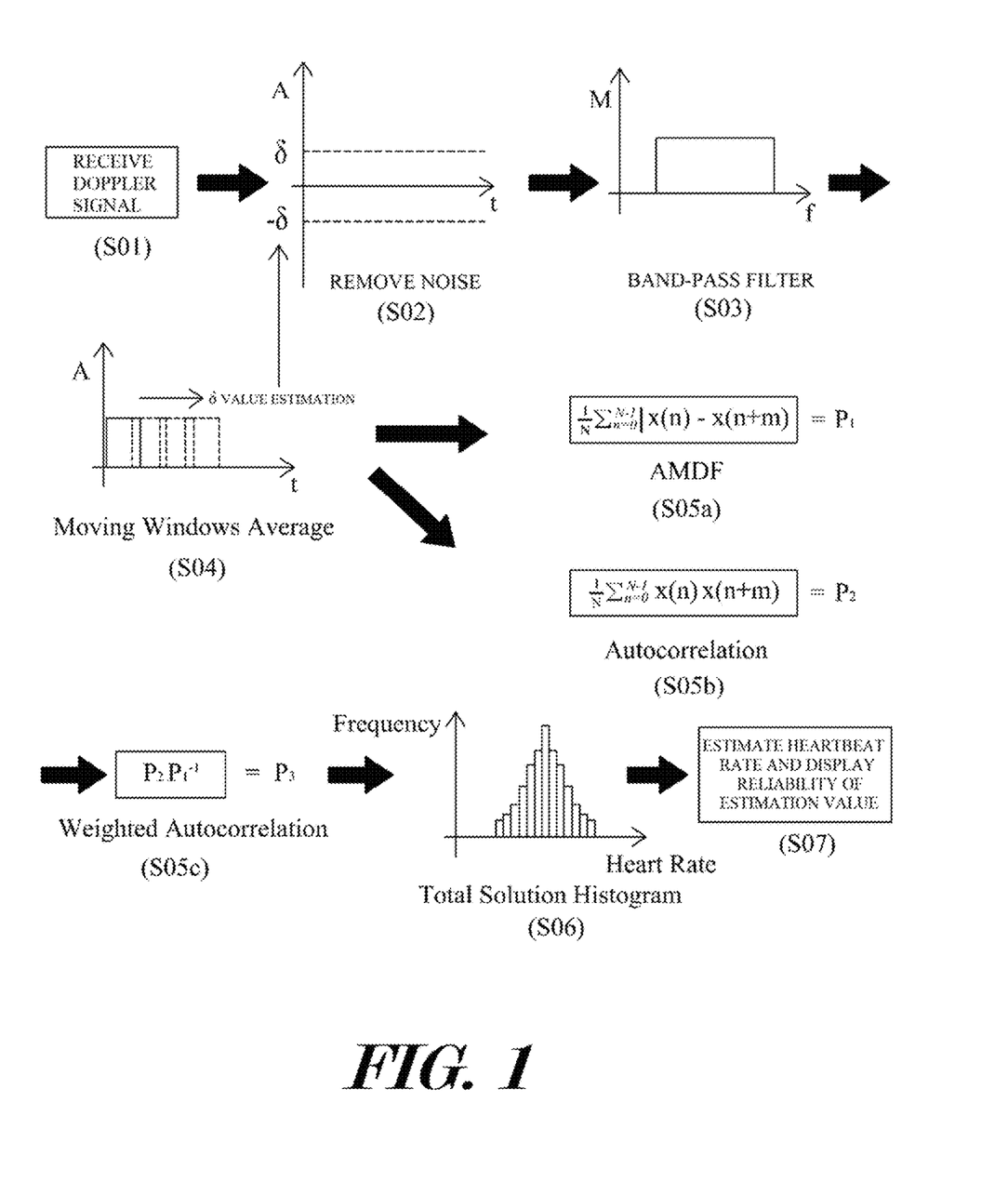
FIG. 1 is a view illustrating a heartbeat detection signal processing method of an ultrasonic Doppler fetus monitoring device according to an embodiment of the present invention.
Figure 2:
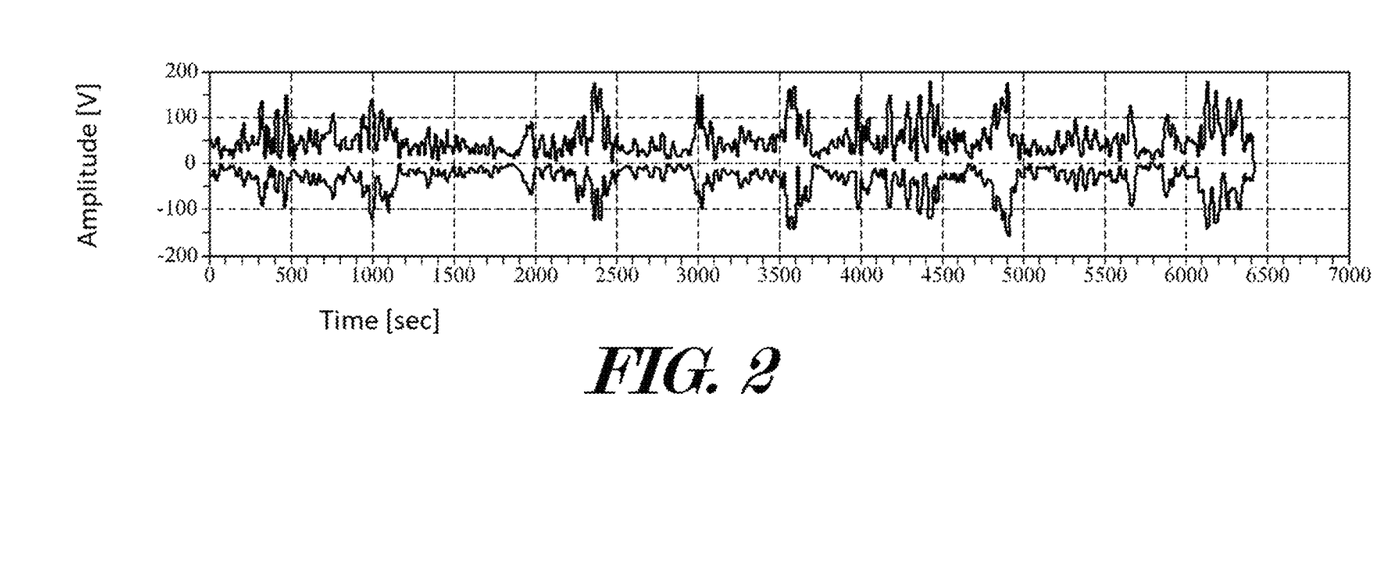
FIG. 2 is a graph showing a Doppler signal according to heartbeat in a heartbeat detection signal processing method of an ultrasonic Doppler fetus monitoring device according to an embodiment of the present invention.
Figure 3:
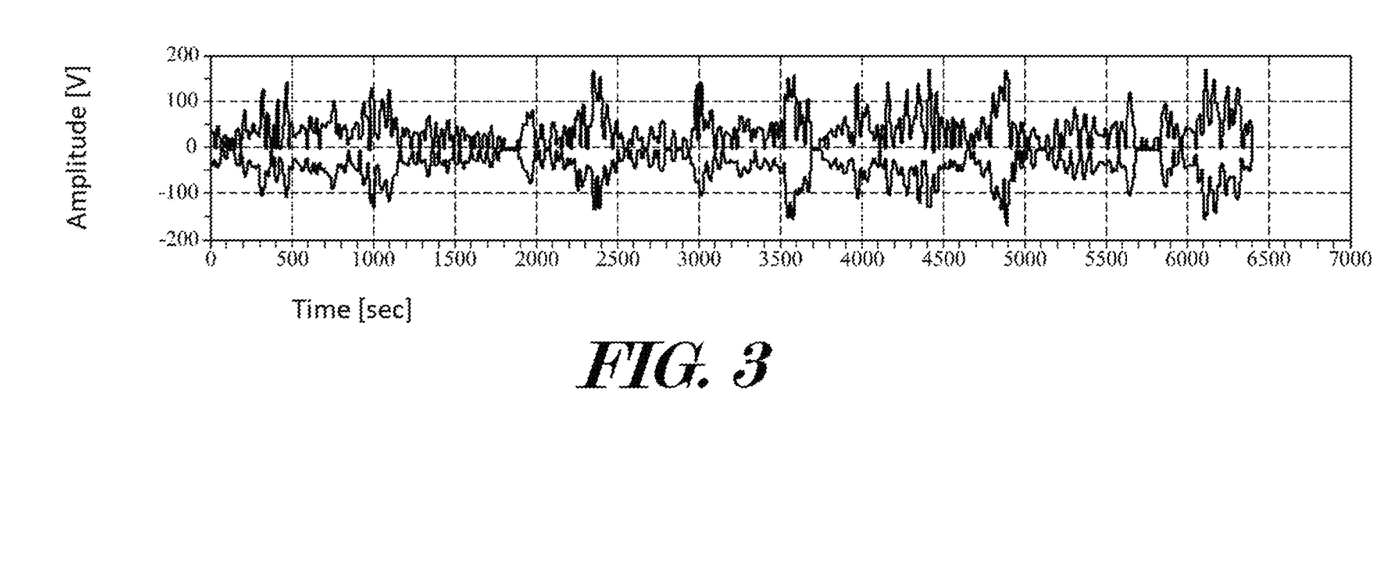
FIG. 3 is a graph showing a signal in which a noise threshold of a signal estimated based on a moving window average result after a band-pass filter is removed in heartbeat detection signal processing method of an ultrasonic Doppler fetus monitoring device according to an embodiment of the present invention.
Figure 4:
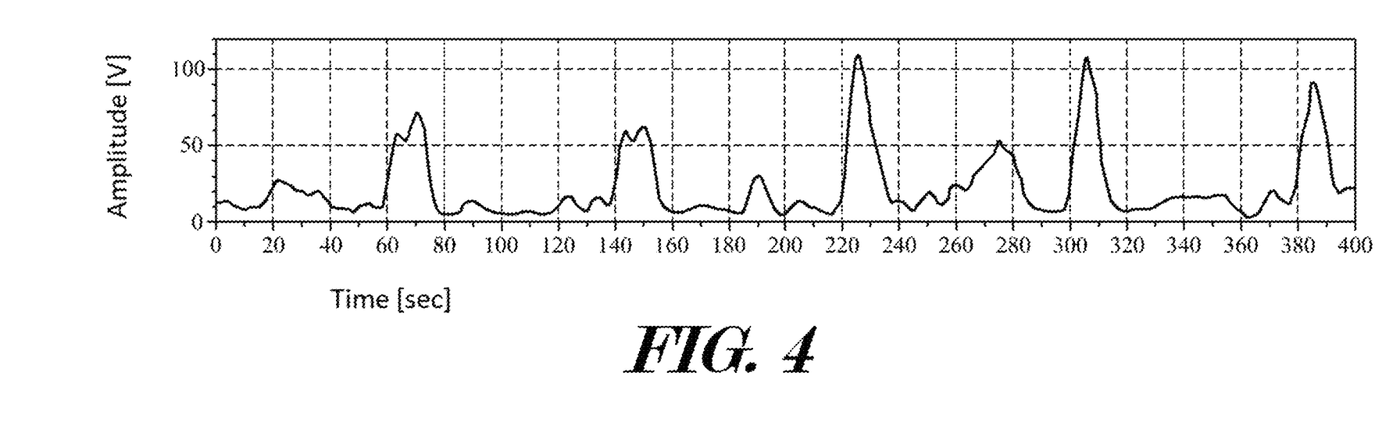
FIG. 4 is a graph showing a Moving Window Average result in a heartbeat detection signal processing method of an ultrasonic Doppler fetus monitoring device according to an embodiment of the present invention.

In describing a heartbeat detection signal processing method of an ultrasonic Doppler fetus monitoring device according to an embodiment of the present invention with reference to FIG. 1, the method includes receiving (S01) a Doppler signal according to a heartbeat, after removing (S02) a noise from the received Doppler signal, after transmitting (S03) it through a band-pass filter, and preprocessing (S04) it to extract an effective signal of the Doppler signal using a moving window average to select a signal of the input Doppler shifted frequency band. In this process, the Doppler signals as shown in FIG. 2 are preprocessed as shown in FIG. 3, respectively.

Figure 13:
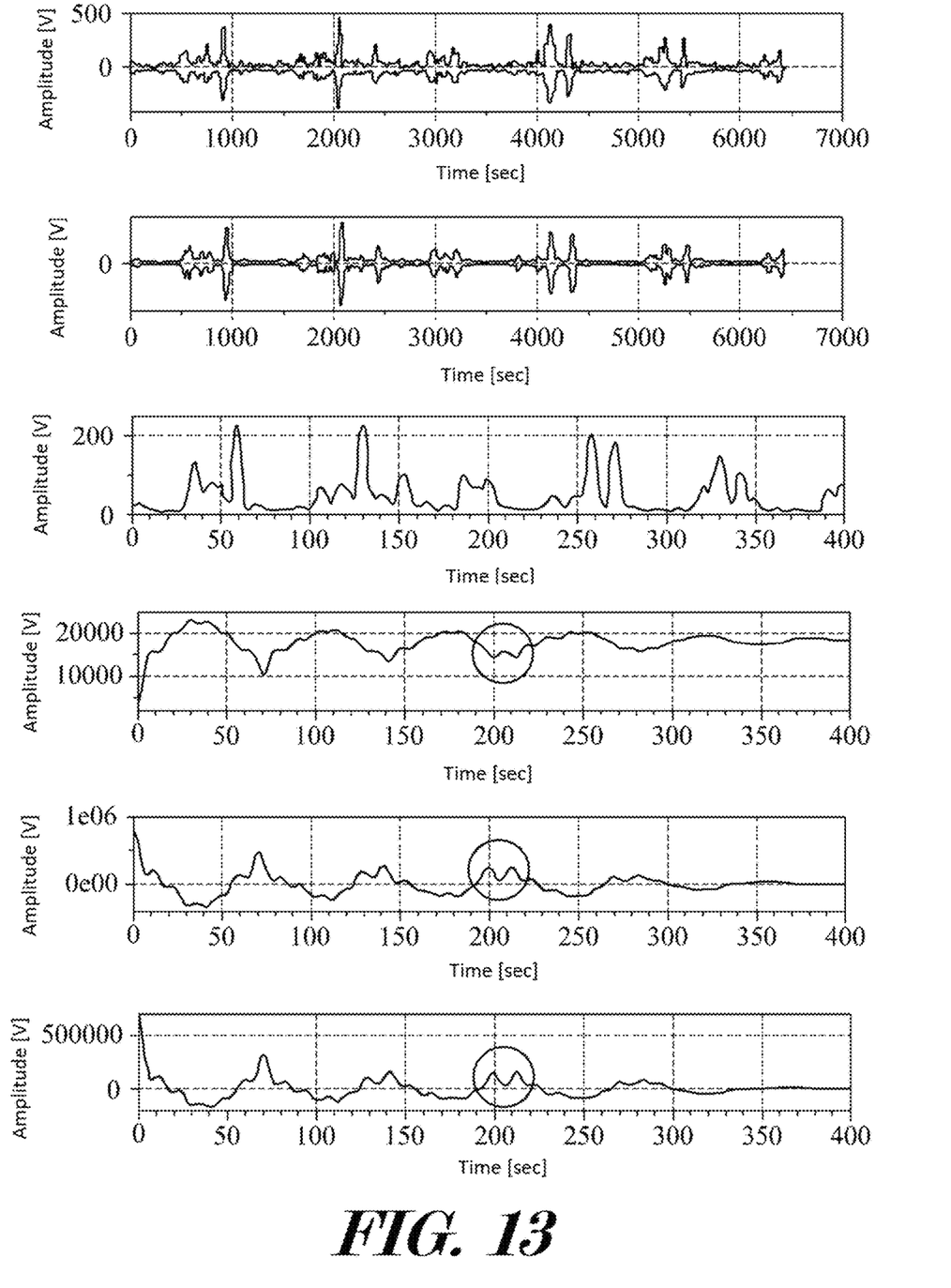
FIG. 13 is a view illustrating a problem of dual peak generation according to an embodiment of the present invention.
Figure 14:
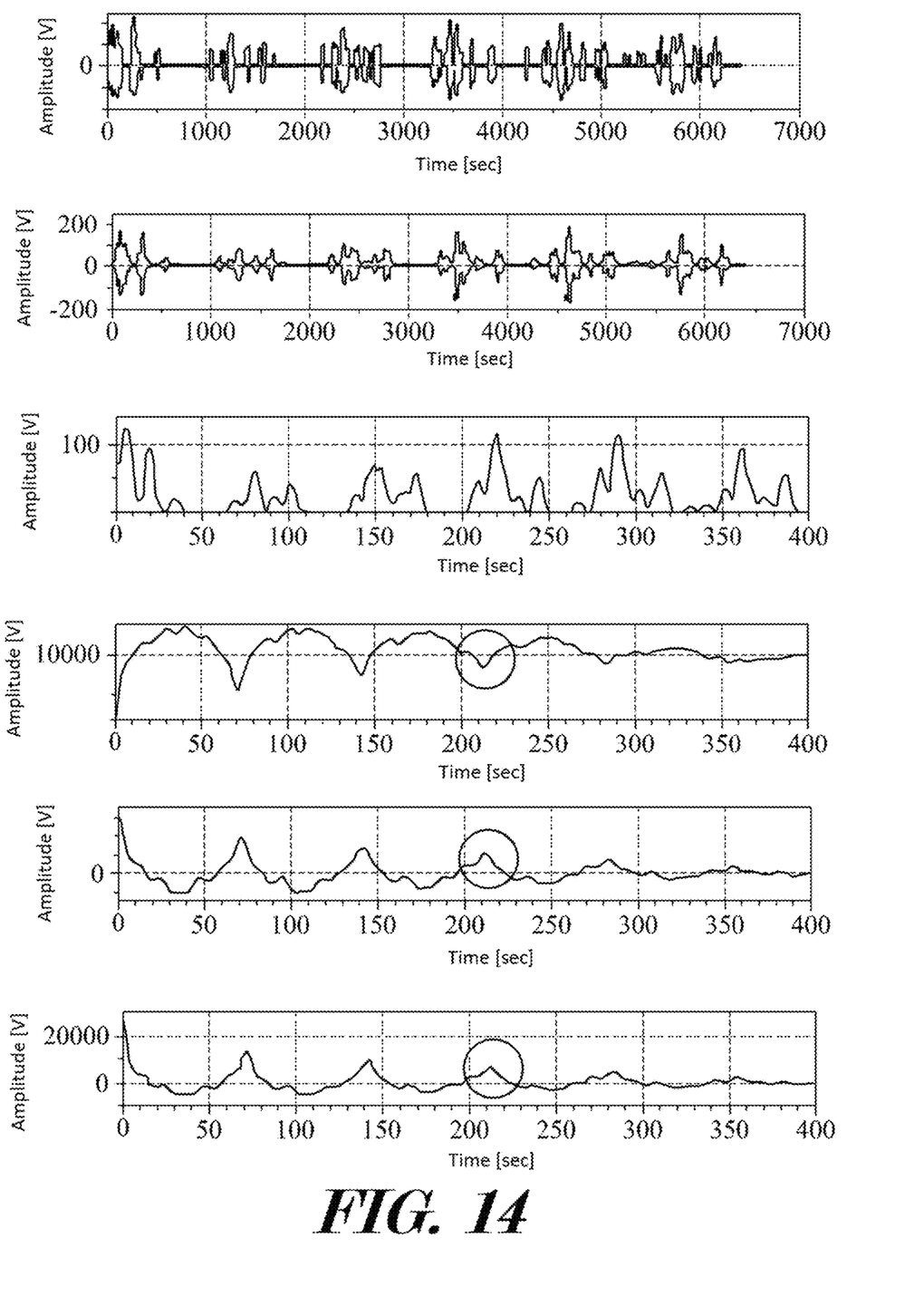
FIG. 14 is a graph showing a clear single peak when estimating a threshold of a noise signal in preprocessing (S04) by using a Moving Window Average (S04) and then, using the threshold as a noise signal threshold in removing (S02) the noise again in a heartbeat detection signal processing method of an ultrasonic Doppler fetus monitoring device according to an embodiment of the present invention.

On the other hand, as in the conventional signal processing method, when noise is removed by using a fixed noise threshold instead of noise reduction using the effective signal and the noise threshold value, there is a problem that a preprocessed signal using a moving window average generates a double peak of a similar size as a waveform in a portion indicated by a circle in FIG. 13, thereby distorting the result frequently. Accordingly, in relation to a heartbeat detection signal processing method of an ultrasonic Doppler fetus monitoring device according to an embodiment of the present invention, as shown in FIG. 1, after a threshold of the noise signal is estimated in the performing of the preprocessing (S04) using the moving window average, it may be used as the noise signal threshold in the removing (S02) of the noise. In other words, as described above, in the smoothing process of the signal for performing the preprocessing (S04) to extract the effective signal of the Doppler signal using the moving window average, by estimating a noise level sensitive to peak detection and using the noise level as a threshold of valid signal-to-noise of the next signal having a high temporal correlation, a single peak may be clearly detected as in the waveform at the portion indicated by the circle in FIG. 14.

Thereafter, detecting the periodicity of a signal varying according to the heartbeat from the selected signal by using various signal processing methods is performed. In this case, as shown in FIG. 1, calculating a fetal heartbeat rate is performed through an Average Magnitude Difference Function (AMDF) (S05a) having a waveform shown in FIG. 5, an Autocorrelation Function (S05b) having a waveform shown in FIG. 6, and a weighted autocorrelation function (S05c) having a waveform shown in FIG. 7 using the Average Magnitude Difference Function (AMDF) and the Autocorrelation Function to detect a periodicity of a signal that varies according to the heartbeat from the selected signal.

Figure 5:
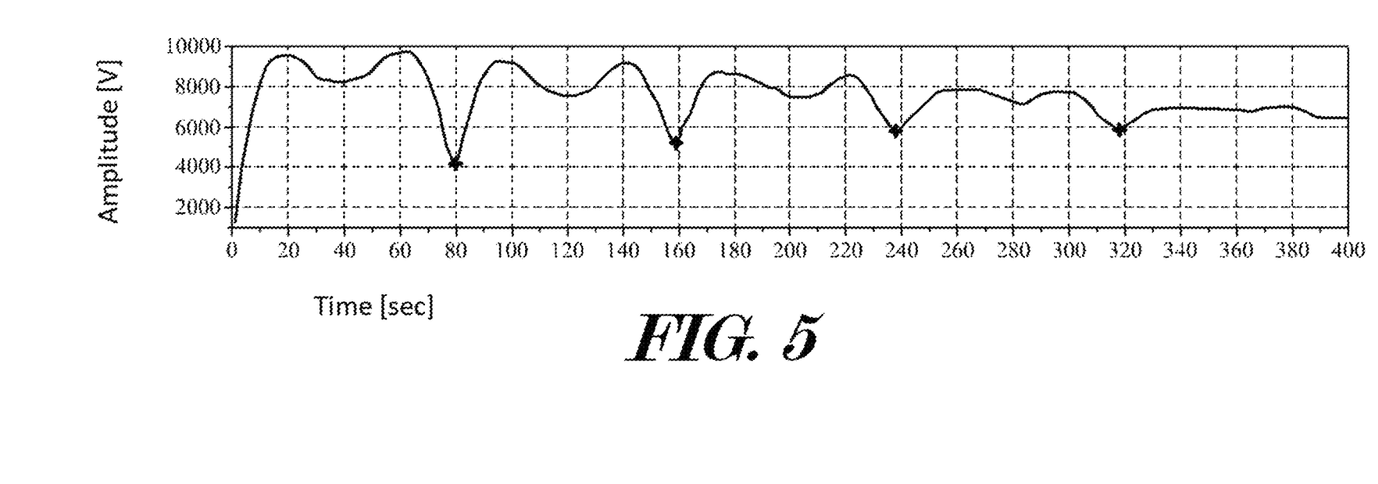
FIG. 5 is a graph showing an AMDF result in a heartbeat detection signal processing method of an ultrasonic Doppler fetus monitoring device according to an embodiment of the present invention.
Figure 6:
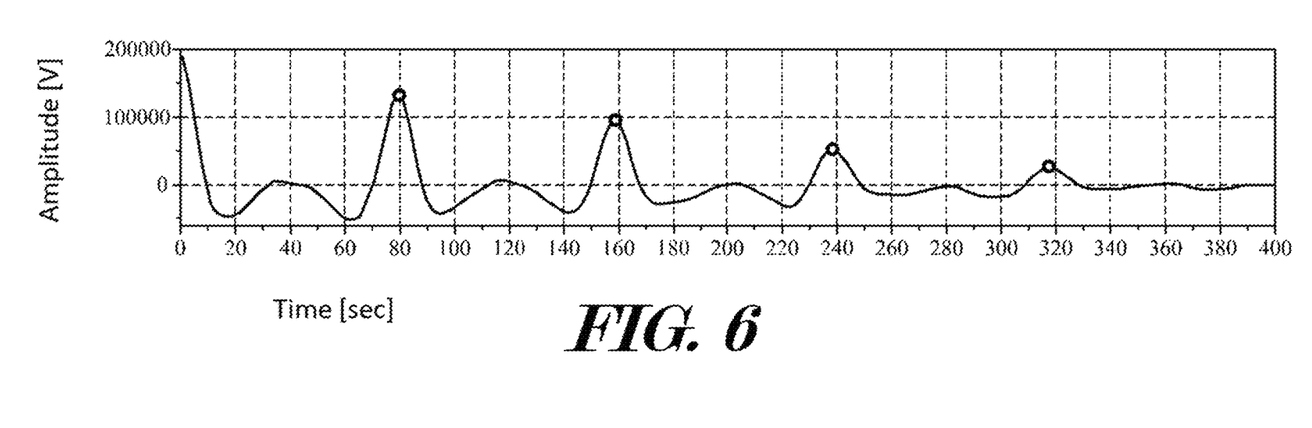
FIG. 6 is a graph showing an Autocorrelation result in a heartbeat detection signal processing method of an ultrasonic Doppler fetus monitoring device according to an embodiment of the present invention.
Figure 7:
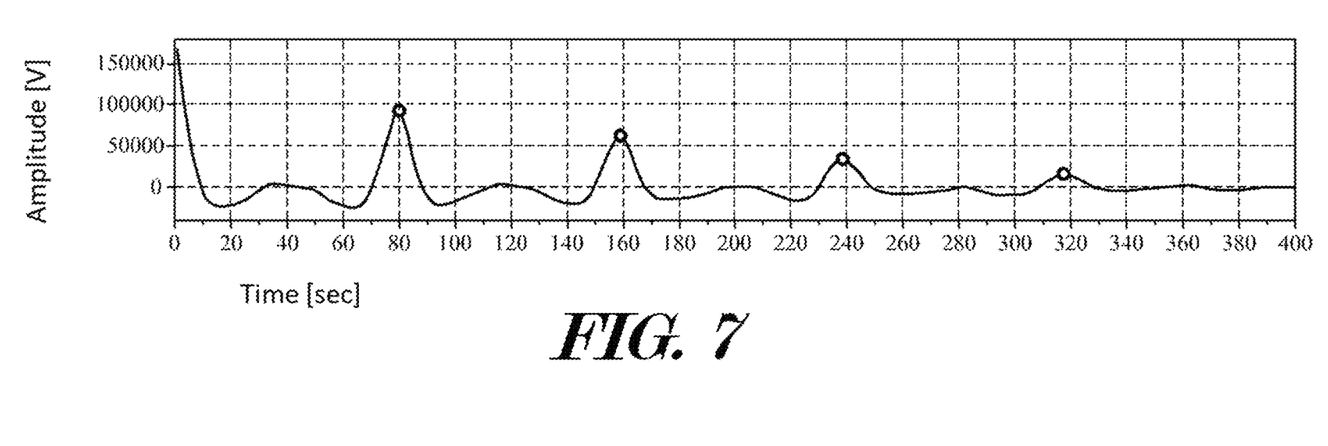
FIG. 7 is a graph showing a Weighted Autocorrelation result in a heartbeat detection signal processing method of an ultrasonic Doppler fetus monitoring device according to an embodiment of the present invention.

At this time, when the AMDF is applied, the waveform of the AMDF is shown opposite to the waveform of the autocorrelation function shown in FIG. 6 as can be seen in FIG. 5. Accordingly, a notch (not a peak) is detected so as to detect a signal period. On the other hand, when only the autocorrelation function is applied, a peak appearing before the fundamental period or a peak appearing after the fundamental period is detected and an erroneous period in which the renewal period is decreased or increased sometimes occurs. Therefore, a weighted autocorrelation function using the AMDF (Average Magnitude Difference Function) and the Autocorrelation Function may be further used.

In this case, the weighted autocorrelation function $P_3$, as shown in FIG. 1, may be determined by multiplying the reciprocal of the average magnitude difference function (AMDF) $P_1$ and the autocorrelation function $P_2$. That is, since the inverse number of the Average Magnitude Difference Function (AMDF) $P_1$ that detects a notch has an opposite peak value at the notch position, when it is multiplied by the autocorrelation function $P_2$ for detecting the peak, the peak value to be detected is further strengthened.

Figure 8:
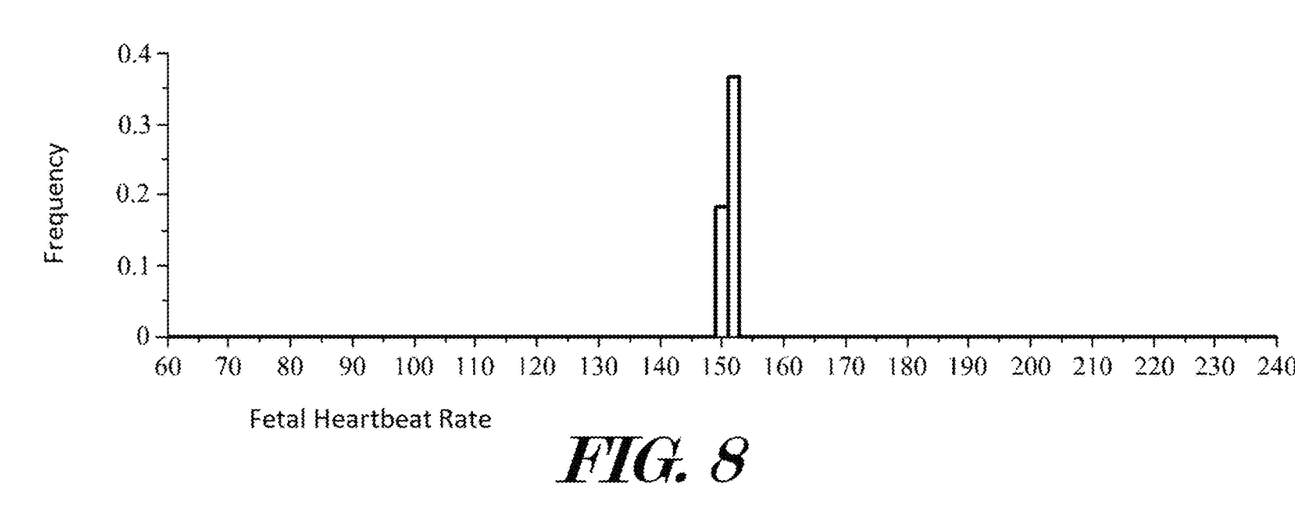
FIG. 8 shows histograms (examples of low variance and high frequency) of all results obtained from AMDF, Autocorrelation, and Weighted autocorrelation results in a heartbeat detection signal processing method of an ultrasonic Doppler fetus monitoring device according to an embodiment of the present invention.
Figure 9:
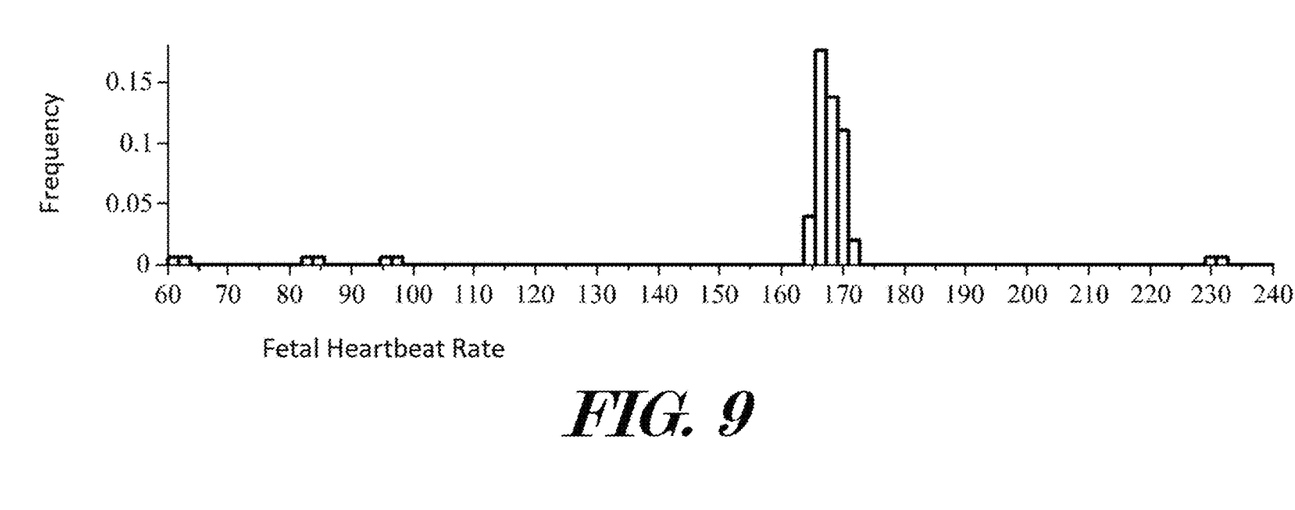
FIG. 9 shows histograms (examples of a case where the maximum frequency value has a somewhat large variance value) of all results obtained from AMDF, Autocorrelation, and Weighted autocorrelation results in a heartbeat detection signal processing method of an ultrasonic Doppler fetus monitoring device according to an embodiment of the present invention.
Figure 10:
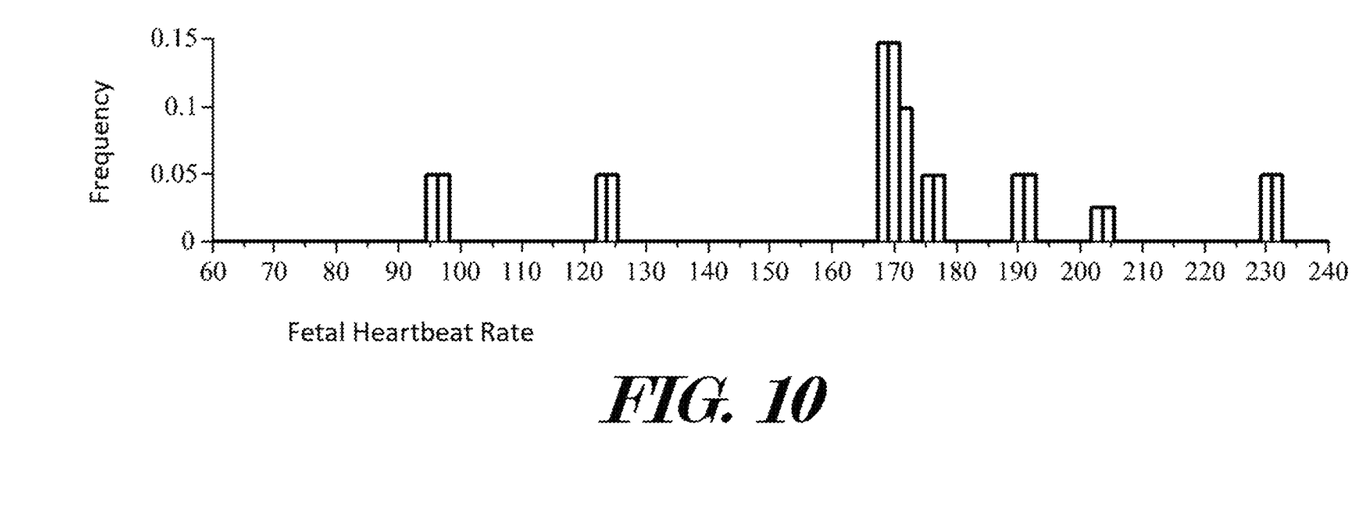
FIG. 10 shows histograms (other examples of a case where the maximum frequency value has a somewhat large variance value) of all results obtained from AMDF, Autocorrelation, and Weighted autocorrelation results in a heartbeat detection signal processing method of an ultrasonic Doppler fetus monitoring device according to an embodiment of the present invention.

Then, as shown in FIG. 1, by using the heartbeat rate calculated by the Average Magnitude Difference Function (AMDF), the autocorrelation function, and the weighted autocorrelation function, configuring (S06) a histogram is performed as shown in FIGS. 8 to 10. In this case, according to the maximum frequency value in the histogram (about 152 in FIG. 8, about 166 in FIG. 9, and 167 and 170 in FIG. 10), fetal heartbeat rates are estimated and displayed (S07). That is, in addition to considering various periodic measurement algorithms, this is analyzed more probabilistically/statistically to obtain a true value.

In this case, as the fetal heartbeat rate is estimated according to the maximum frequency value in the histogram in order to know the measurement reliability of the determined value together, it may further perform calculating the measurement reliability and displaying the measurement reliability together. The measurement reliability may be calculated by various methods, and it may calculate and display a δ value determined according to the following equation as the measurement reliability.

[Equation] where the δ represents the standard deviation and $\bar{x}$ is the mean value of the data set and X is a data point from the data set and N is the total number of data points.

$$\delta = \sqrt{\frac{\sum |x - \bar{x}|^2}{N}}$$

Figure 11:
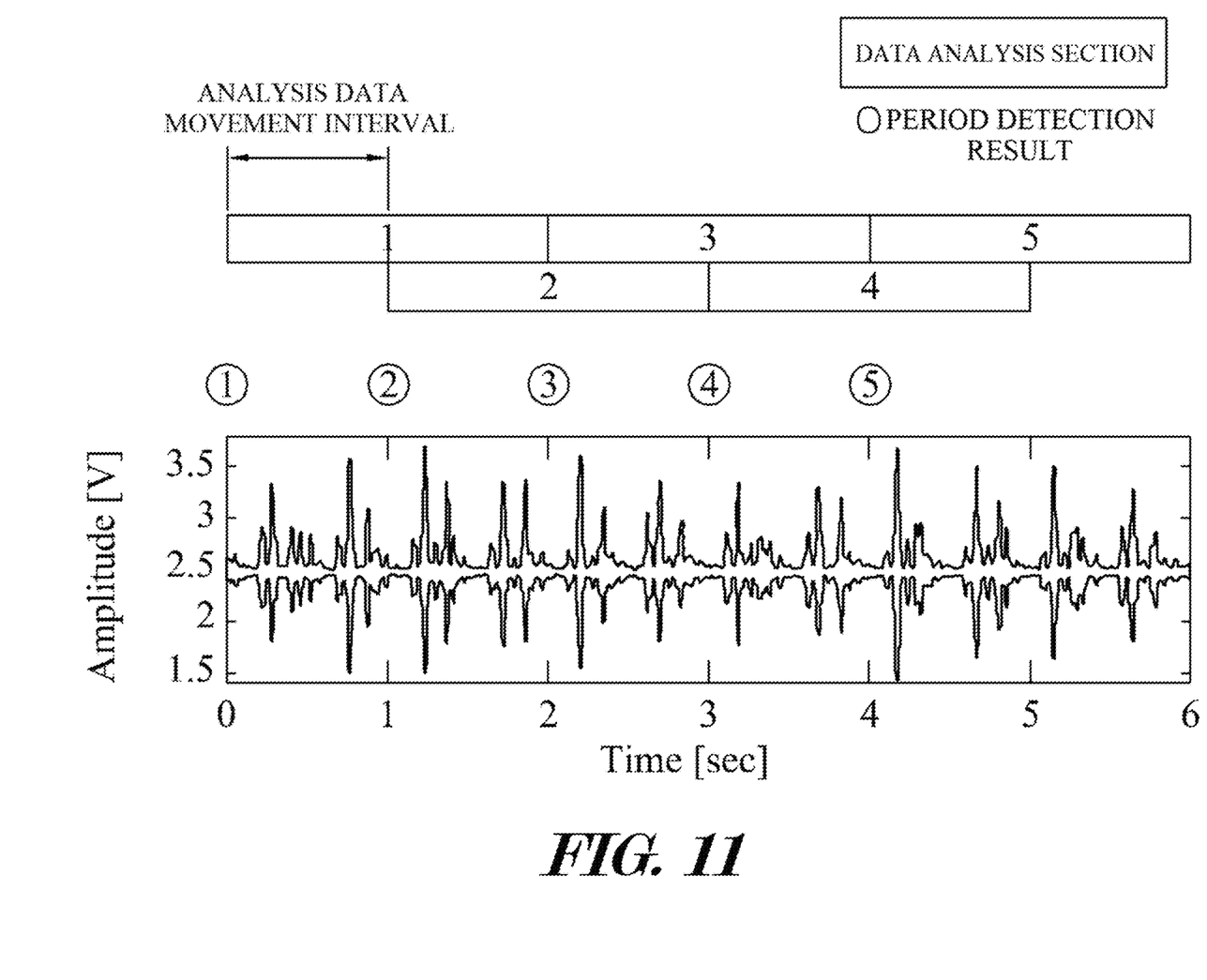
FIG. 11 is a view for explaining an analysis section setting method in a heartbeat detection signal processing method of an ultrasonic Doppler fetus monitoring device according to the embodiment of the present invention.
Figure 12:
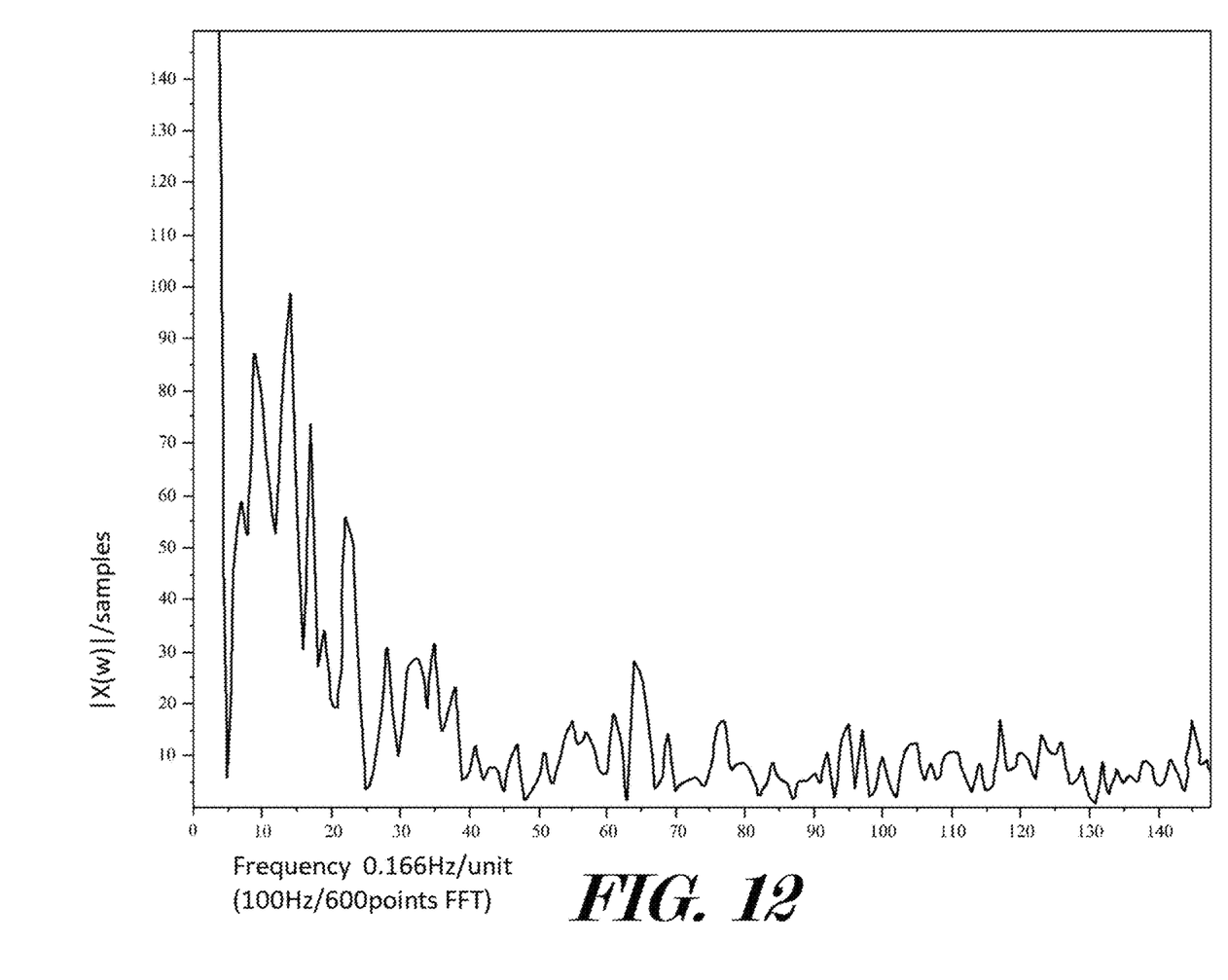
FIG. 12 is a graph showing a result of calculating a distribution and size according to a frequency band of the heartbeat rate through spectrum analysis in a heartbeat detection signal processing method of an ultrasonic Doppler fetus monitoring device according to an embodiment of the present invention.

Meanwhile, in order to detect peaks from continuous audio Doppler signals by applying the average magnitude difference function (AMDF), the autocorrelation function, and the weighted autocorrelation function, a data analysis section is set as shown in FIG. 11, and a peak is detected through autocorrelation of a signal corresponding to the data analysis section. Also, a peak is continuously detected while moving the data analysis section at a predetermined interval, and a signal period is detected using the detected peak-to-peak interval.

Generally, the size of the data analysis section is set to at least twice the signal period to be searched. On the other hand, when the size of the analysis section is set to be large enough to include several signal periods, it is impossible to detect a plurality of peaks existing in the analysis region, and when the size of the analysis section is set to be small enough not to include one signal period, the peak detection fails.

Accordingly, in order to increase the accuracy of peak detection, it is necessary to set the window size by appropriately setting the minimum period and the maximum period.

On the other hand, the size and the movement interval of the analysis section have a great influence on the calculation accuracy as well as the detection accuracy. For example, as the size of the analysis section increases, the influence of the noise signal decreases, but the calculation amount increases. Also, for example, if the movement interval of the analysis section is reduced, the resolution of the detection result increases, while the amount of calculation increases.

Therefore, the size and movement interval of the analysis section need to be varied in consideration of the amount of calculation and the sensitivity of heartbeat rate variability.

Accordingly, the fetal heartbeat detection device according to an embodiment of the present invention may dynamically vary the size and the movement interval of the current analysis section to allow continuous beat-to-beat detection based on the signal period of the previous signal.

For this, the window size and the movement interval for peak detection may be updated dynamically based on the previous signal period.

On the other hand, the heartbeat rate change measured for a predetermined relatively long continuous time (about 5 minutes to 10 minutes) is spectrum-analyzed through frequency analysis, and the distribution and size of the dynamic change according to the frequency band (VLF, LF, MF, and HF) of the heartbeat rate change is known, so that information useful for fetal health diagnosis (e.g., autonomic nervous system response) may also be obtained. For this, the window size may be set at intervals of 5 to 10 minutes, and a distribution and a size according to a frequency band of the heartbeat rate may be further detected by spectrum-analyzing each heartbeat rate calculated through the Average Magnitude Difference Function (AMDF), the Autocorrelation Function, and the Weighted Autocorrelation Function, through fast Fourier transform (FFT).

As described above, according to the present invention, in order to improve fetal detection accuracy and reduce fetal heartbeat detection error, through a heartbeat detection signal processing method of an ultrasonic Doppler fetus monitoring device using a preprocessing method, a peak detection method, and probabilistic estimation and reliability estimation, in addition to considering various periodic measurement algorithms for waveforms extracted from a fetal heart sound measuring device with respect to a fetal heartbeat rate detection device, this is further analyzed probabilistically/statistically to obtain accurate true values and it is possible to calculate the reliability of the estimate for each estimate result.

In addition, in the present invention, the measured heart rate change is spectrum-analyzed through frequency analysis using FFT with a window of 5 to 10 minutes in size, and the distribution and size of the dynamic change according to the frequency band (VLF, LF, MF, and HF) of the heart rate change is known so that useful information for fetal health examination may be obtained together.

In the above, optimal embodiments have been disclosed in the drawings and specification. Although specific terms have been used herein, they are used for purposes of illustration only and are not intended to limit the scope of the invention as defined in the claims or the claims. Therefore, those skilled in the art will understand that various modifications and equivalent embodiments are possible without departing from the scope of the present invention. Accordingly, the true scope of the present invention should be determined by the technical idea of the appended claims.

What is claimed is:

1. A heartbeat detection signal processing method of an ultrasonic Doppler fetus monitoring device that transmits an ultrasonic wave to an abdomen of a pregnant woman and detects a fetal heartbeat rate by receiving a Doppler variation signal generated according to the fetal heartbeat, wherein each step of the method is performed by the ultrasonic Doppler fetus monitoring device, the method comprising the following steps in the following sequential order:

transmitting an ultrasonic wave from the ultrasonic Doppler fetus monitoring device;

receiving (S01) a first Doppler signal according to a fetal heartbeat, removing (S02) a noise from the received first Doppler signal, transmitting (S03) the first Doppler signal through a band-pass filter, and a preprocessing step (S04) to extract an effective signal of the first Doppler signal using a moving window average to select a signal of an input Doppler shifted frequency band by estimating a noise level sensitive to peak detection and using that estimated noise level as a noise level threshold of valid signal-to-noise of a next Doppler signal having a high temporal correlation wherein the noise level threshold is adaptive and configured to change based on prior Doppler signals;

calculating a fetal heartbeat rate through an Average Magnitude Difference Function (AMDF) (S05a); and an Autocorrelation Function (S05b), and next determining a weighted autocorrelation function (S05c) using a product from multiplying a reciprocal of the Average Magnitude Difference Function (AMDF) and the Autocorrelation Function;

configuring (S06) a histogram using output from the Weighted Autocorrelation Function;

estimating and determining the fetal heartbeat rate according to a maximum frequency value in the histogram (S07);

displaying the fetal heartbeat rate; and wherein after the noise level threshold is estimated in the preprocessing step (S04) using the moving window average, the noise level threshold is used again as the noise level threshold in removing noise for a second Doppler signal in step (S02) and the steps (S02) through (S07) are repeated and the noise level threshold is therefore dynamic and not fixed and the first Doppler signal is a separate and distinct signal from the second Doppler signal and each are received at different points in time.

2. The method of claim 1, further comprising calculating and displaying, via the ultrasonic Doppler fetus monitoring device, a measurement reliability of the fetal heartbeat rate as a 45 value determined according to the following equation in the histogram and displays the fetal heartbeat rate $$\delta = \sqrt{\frac{\sum |x - \bar{x}|^2}{N}}.$$ [Equation]

3. The method of claim 2, wherein the ultrasonic Doppler fetus monitoring device dynamically updates a window size and a movement interval for peak detection based on a previous signal period and displays the fetal heartbeat rate.

4. The method of claim 2, wherein a window size is set at fixed constant intervals with a minimum period and a maximum period, wherein a distribution and a size according to a frequency band calculated through the Average Magnitude Difference Function (AMDF), the Autocorrelation Function, and the Weighted Autocorrelation Function, through fast Fourier transform (FFT) and wherein the ultrasonic Doppler fetus monitoring displays the fetal heartbeat rate.

5. The method of claim 1, wherein the histogram plots a frequency of determined fetal heartbeat rates on a y-axis and the fetal heartbeat rate on an x-axis.

* * * * *